US00PP09867P

United States Patent [19]

Westhoff

[11] Patent Number: Plant 9,867

[45] Date of Patent: Apr. 22, 1997

[54] SCAEVOLA PLANT NAMED FANCY

[75] Inventor: Wilhelm Westhoff, Südlohn, Germany

[73] Assignee: J+H Westhoff, Sudlohn, Germany

[21] Appl. No.: 592,657

[22] Filed: Jan. 26, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 7,929 8/1992 Rother ..... Plt./68.1

*Primary Examiner*—James R. Feyrer
*Attorney, Agent, or Firm*—C. A. Whealy

[57] ABSTRACT

A distinctive cultivar of Scaevola plant named Fancy, characterized by its symmetrical, spreading and compact growth habit with short internodes; fast-growing long branches; long leaves; early flowering; numerous flowers per plant; weather-resistant and long-lasting flowers; large flower size; intense blue-violet petal color with narrow white band at petals' base and yellow area at top of flower throat; and pleasant fragrance.

2 Drawing Sheets

The present invention relates to a new and distinct cultivar of Scaevola plant, botanically known as *Scaevola aemula*, and hereinafter referred to by the cultivar name Fancy.

The new cultivar is a product of a planned breeding program conducted by the inventor in Südlohn, Germany. The objective of the breeding program was to develop varieties that are more compact in growth habit, flower early, and have numerous flowers per plant.

The new cultivar originated from a cross made by the inventor of a wild form of *Scaevola aemula* as the male or pollen parent with the nonpatented *Scaevola aemula* variety Lazuli as the female or seed parent.

The cultivar Fancy was discovered and selected by the inventor in April, 1993, as a flowering plant within the progeny of the stated cross in a controlled environment in S üdlohn, Germany. Subsequent asexual reproduction of the new cultivar by terminal cuttings taken at Südlohn, Germany, has shown that the unique features of this new Scaevola are stabilized and reproduced true to type in successive generations of asexual reproduction.

The following traits have been repeatedly observed and are determined to be the unique characteristics of Fancy. These characteristics in combination distinguish the new Scaevola as a new and distinct cultivar:

1. Symmetrical, spreading and compact growth habit with short internodes. Plant shape is appropriate for hanging basket containers and chemical growth retardant treatments are usually not required.
2. Fast-growing long branches.
3. Long leaves.
4. Early flowering.
5. Numerous flowers per plant.
6. Weather-resistant and long-lasting flowers.
7. Large flower size.
8. Intense blue-violet petal color with narrow white band at petals' base and yellow area at top of flower throat.
9. Pleasant fragrance.

In comparison to the parents of the new Scaevola, plants of Fancy are more compact in growth habit, have larger flowers, and flowers are darker blue-violet in color.

The new Scaevola is most similar to the *Scaevola aemula* cultivar Blue Wonder, disclosed in U.S. Plant Pat. No. 7,929. Fancy differs from Blue Wonder in the following characteristics:

1. The start of flowering occurs earlier on plants of Fancy compared to plants of Blue Wonder.

2. Flowers of plants of Fancy are larger than flowers of plants of Blue Wonder.
3. Flowers of plants of Fancy are slightly lighter in flower color compared to flowers of plants of Blue Wonder.
4. Flowers of plants of Fancy have a much narrower white band at the base of the petals compared to flowers of plants of Blue Wonder.

A detailed comparison of Fancy and Blue Wonder plants appears in Chart A at the end of the specification.

The new Scaevola has not been observed under all possible environmental conditions. The phenotype may vary significantly with variations in environment such as temperature, light level and daylength, without, however, any variance in genotype.

The accompanying colored photographs illustrate the overall appearance and flower color of the new Scaevola, showing the colors as true as it is reasonably possible to obtain in colored reproductions of this type.

The first photograph comprises a top perspective view of a typical plant of the new Scaevola grown in Südlohn, Germany.

The second photograph comprises a close-up view of a typical flower stem. The flower color appears lighter than the actual flower color in this photograph due to light reflectance.

The following observations, measurements, values, and comparisons describe plants grown in Südlohn, Germany.

In the following description, color references are made to The Royal Horticultural Society Colour Chart except where general terms of ordinary dictionary significance are used.

Botanical classification: *Scaevola aemula* cultivar Fancy.

Parentage:

*Male or pollen parent.*—Wild form of *Scaevola aemula.*

*Female or seed parent.*—*Scaevola aemula* variety Lazuli.

Propagation:

*Type cuttings.*—Terminal cuttings or by tissue culture.

*Rooting habit.*—Numerous, fibrous, and freely branching.

Plant description:

*Form.*—Symmetrical and spreading, suitable for hanging basket containers.

*Growth habit.*—Compact yet moderately vigorous. Axillary shoots develop at leaf axils on non-flowering stems. Leaf axils on flowering stems do not produce axially shoots.

*Axillary shoot description.*—Aspect; Semi-upright, prostrate or semi-pendulous. Length: Generally 50 cm. Internode length: 1 to 2 cm. Diameter: 3 to 4 mm. Color: Olive green to purple depending on anthocyanin level. Texture: Smooth, glabrous.

*Foliage description.*—Size: Length: 6 to 8 cm. Width: 2 to 3 cm. Shape: Spatulate. Margin: Slightly serrated at leaf base and becoming strongly serrated towards leaf tip. Color, upper side: 137B to 137C.

Flower description:

*Flower type and shape.*—Semi-circular, fan-shaped flowers with five petals fused at their bases to form a tubular flower throat. Flower throat open along the upper side exposing reproductive organs. Flowers sessile.

*Flower arrangement.*—Flowers arise from leaf axils with one flower per axil.

*Perianth.*—Aspect: Fan-shaped, flat. Diameter: 3.5 to 4 cm. Venation: Parallel to midrib of each petal. Color: Upper surface: Violet-blue, 90D. Under surface: Violet-blue, 90D. Venation: Darker violet-blue, 90C.

*Petals.*—Quantity: Five. Shape: Oblanceolate. Tips: Mucronate.

*Flower throat.*—Length: About 1.5 cm. Color of throat opening: Narrow white band at base of petals with yellow area at top of flower throat and purple stripes radiating from the throat.

*Reproductive organs.*—Ovary: Shape: Elongate. Length: 1 to 2 mm. Color: Green. Pistil: Appearance: Broad with purplish hairs 2 mm in length. Aspect: Slightly bent. Length: 1.2 to 1.5 cm. Tip: Bent downwards. Color: Upper surface: Purple. Lower surface: Green. Tip: Yellowish white. Anthers: Length: 1 to 2 mm. Color: Initially yellow and becoming brown with development. Filaments: Protrude from flower throat and are 3 to 5 mm in length.

Disease resistance: No resistance or susceptibility to diseases observed.

Weather tolerance: Very tolerant of rain and adverse weather conditions, flowers long-lasting.

Seed production: Seed production is generally not observed.

CHART A

| CHARACTERISTIC | FANCY | BLUE WONDER |
|---|---|---|
| Start of flowering | Early | Later |
| Flower size | 3.5 to 4 cm | 2.5 to 3 cm |
| Perianth color | 90D | 88B |
| White band at petals' base | Very small, sometimes inconspicuous | Broad, conspicuous |

It is claimed:

1. A new and distinct Scaveola plant named Fancy, as illustrated and described.

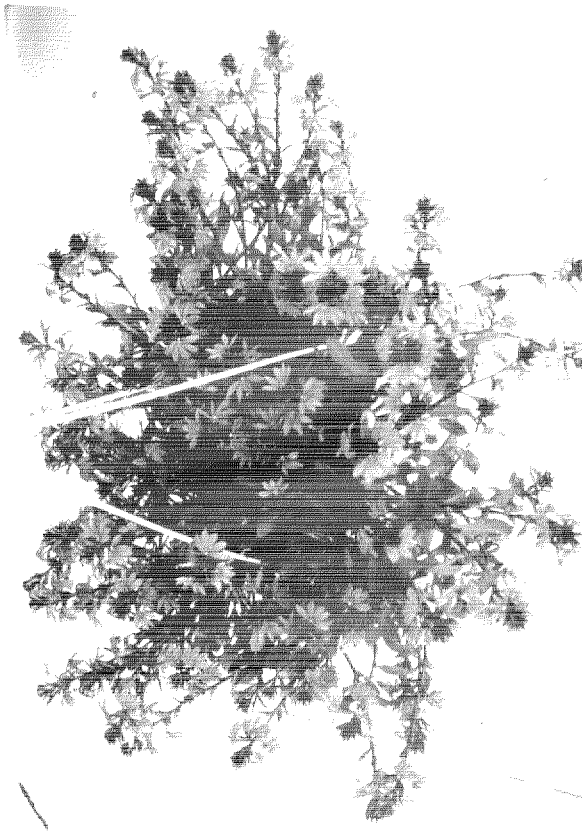

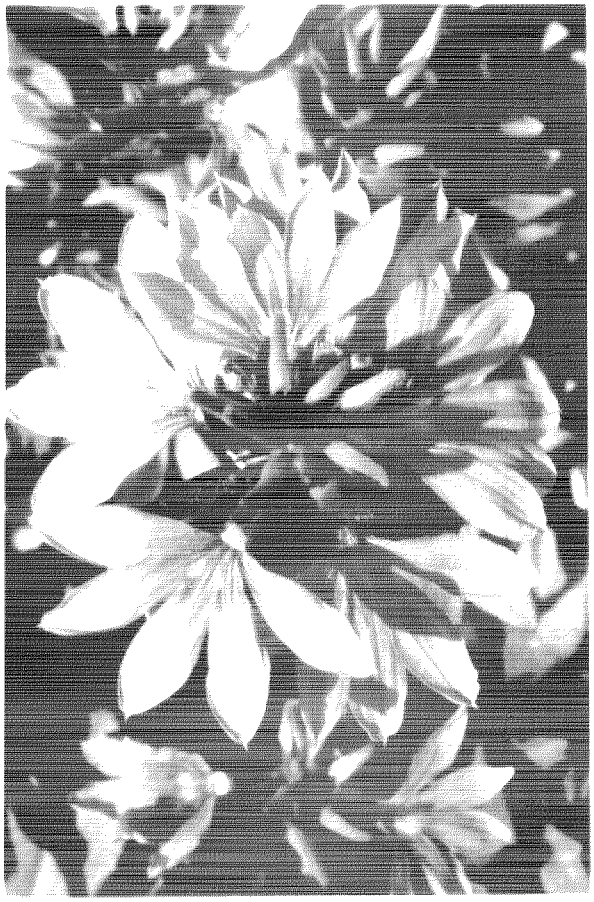

* * * * *